(12) United States Patent
Arayama et al.

(10) Patent No.: US 9,801,764 B2
(45) Date of Patent: Oct. 31, 2017

(54) DISPOSABLE WEARING ARTICLE WITH CURVING UNIT

(75) Inventors: Takaya Arayama, Kanonji (JP); Hirotomo Mukai, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 847 days.

(21) Appl. No.: 14/343,373

(22) PCT Filed: Sep. 5, 2012

(86) PCT No.: PCT/JP2012/005617
§ 371 (c)(1),
(2), (4) Date: Jun. 23, 2014

(87) PCT Pub. No.: WO2013/035318
PCT Pub. Date: Mar. 14, 2013

(65) Prior Publication Data
US 2014/0378935 A1 Dec. 25, 2014

(30) Foreign Application Priority Data
Sep. 7, 2011 (JP) .................................. 2011-195207

(51) Int. Cl.
A61F 13/15 (2006.01)
A61F 13/20 (2006.01)
A61F 13/532 (2006.01)
A61F 13/494 (2006.01)
A61F 13/535 (2006.01)

(52) U.S. Cl.
CPC .......... *A61F 13/532* (2013.01); *A61F 13/494* (2013.01); *A61F 13/535* (2013.01)

(58) Field of Classification Search
CPC ........ A61F 13/49001; A61F 2013/5355; A61F 13/494; A61F 13/532; A61F 13/535
See application file for complete search history.

(56) References Cited

U.S. PATENT DOCUMENTS

| | | | |
|---|---|---|---|
| 2004/0054343 A1 | 3/2004 | Barnett et al. | |
| 2006/0184146 A1* | 8/2006 | Suzuki | A61F 13/535 604/358 |
| 2007/0179469 A1* | 8/2007 | Takahashi | A61F 13/535 604/385.101 |

(Continued)

FOREIGN PATENT DOCUMENTS

| | | |
|---|---|---|
| CN | 102076297 A | 5/2011 |
| CN | 103200915 A | 7/2013 |

(Continued)

OTHER PUBLICATIONS

Extended European Search Report dated Mar. 19, 2015, corresponding to European patent application No. 12830205.6.

(Continued)

*Primary Examiner* — Michele M Kidwell
(74) *Attorney, Agent, or Firm* — Hauptman Ham, LLP

(57) ABSTRACT

A disposable wearing article includes a urination region to be in contact with a urination unit of the wearer, a buttocks region to be in contact with buttocks of the wearer, and an absorbent sheet which includes an absorbent polymer sandwiched between liquid-impermeable layers. The absorbent sheet is disposed in the buttocks region but not in the urination region.

13 Claims, 8 Drawing Sheets

(56) References Cited

U.S. PATENT DOCUMENTS

| | | | | |
|---|---|---|---|---|
| 2007/0233029 | A1* | 10/2007 | Jansson | A61F 13/4704 604/380 |
| 2007/0244455 | A1* | 10/2007 | Hansson | A61F 13/4704 604/385.201 |
| 2008/0140042 | A1* | 6/2008 | Mukai | A61F 13/49001 604/385.23 |
| 2010/0004614 | A1* | 1/2010 | Ashton | A61F 13/532 604/367 |

FOREIGN PATENT DOCUMENTS

| | | |
|---|---|---|
| EP | 1723939 A1 | 11/2006 |
| EP | 2184043 A1 | 5/2010 |
| JP | 1-282301 A | 11/1989 |
| JP | H08-508662 A | 9/1996 |
| JP | 2003-093441 A | 4/2003 |
| JP | 2005-137648 A | 6/2005 |
| JP | 2005-312557 A | 11/2005 |
| JP | 2006-346439 A | 12/2006 |
| JP | 2010-075462 A | 4/2010 |
| TW | 576737 B | 2/2004 |
| TW | 200714264 A | 4/2007 |
| WO | 03/026545 A2 | 4/2003 |
| WO | 2011/105108 A1 | 9/2011 |
| WO | 2012/067217 A1 | 5/2012 |

OTHER PUBLICATIONS

Office Action dated Jun. 30, 2015, corresponding to Chinese patent application No. 201280043258.9.

Office Action in TW Application No. 101132352, dated Apr. 27, 2016.

Office Action dated Aug. 11, 2015, corresponding to Japanese Patent Application No. 2011-195207.

International Search Report dated Dec. 11, 2012, in International Application No. PCT/JP2012/005617, filed Sep. 5, 2012.

Written Opinion of the International Searching Authority dated Dec. 11, 2012, in International Application No. PCT/JP2012/005617, filed Sep. 5, 2012.

Office Action dated Oct. 31, 2014, corresponding to Chinese patent application No. 201280043258.9.

Office Action in AU Application No. 2012305780, dated Feb. 17, 2016.

Office Action in GCC Application No. GC 2012-22187 dated May 21, 2017.

* cited by examiner

[Fig. 1]
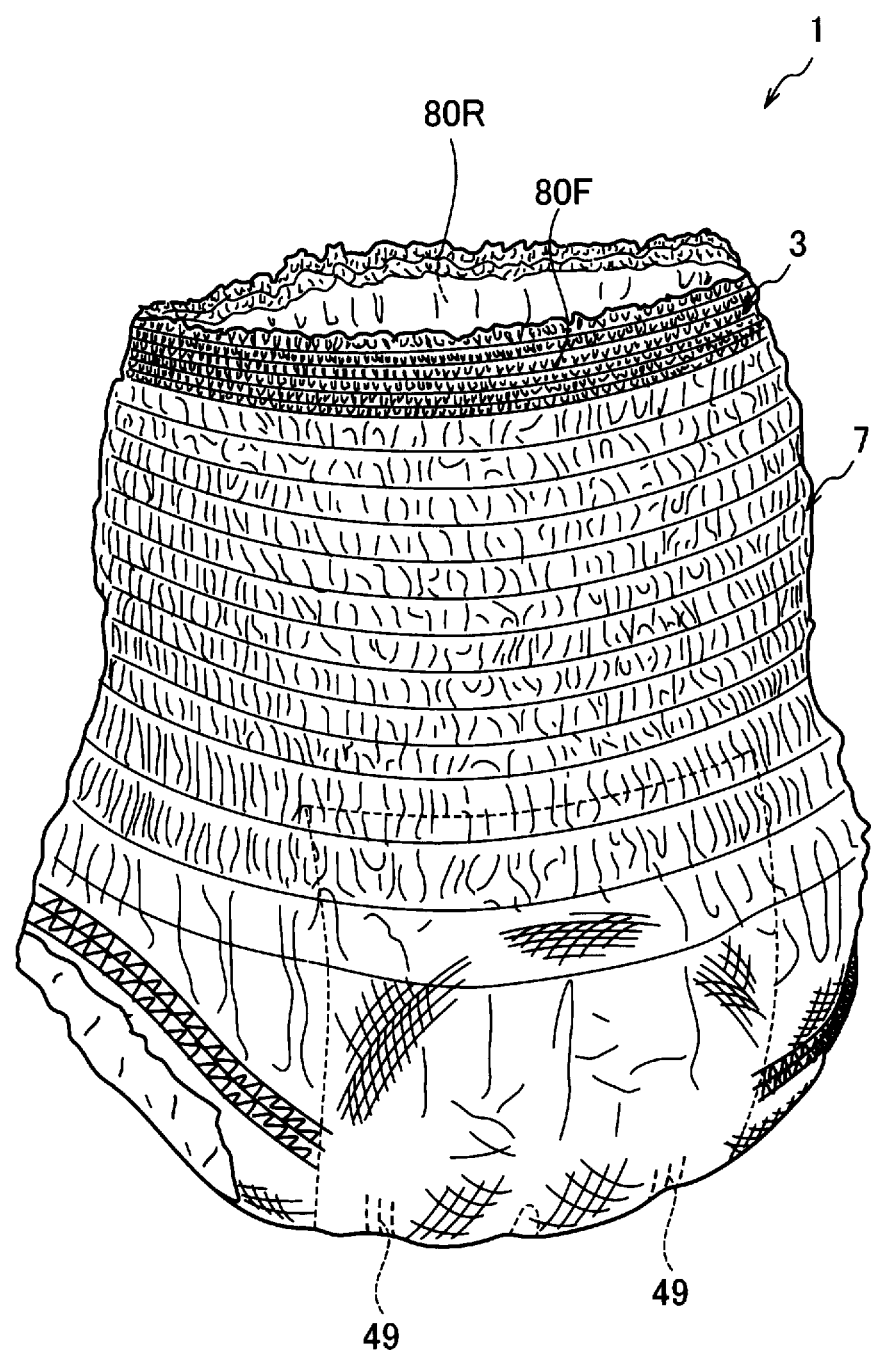

[Fig. 2]
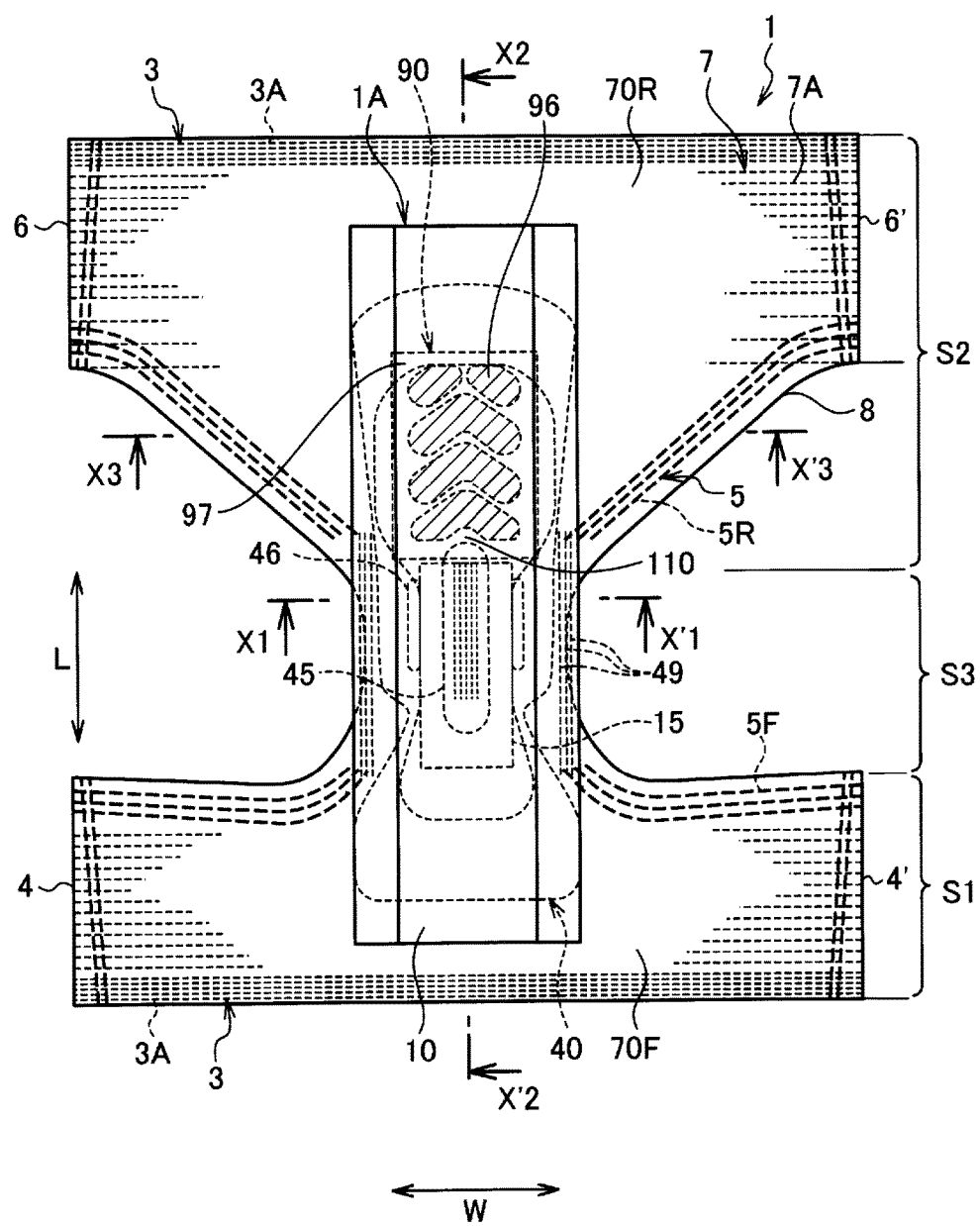

[Fig. 3]
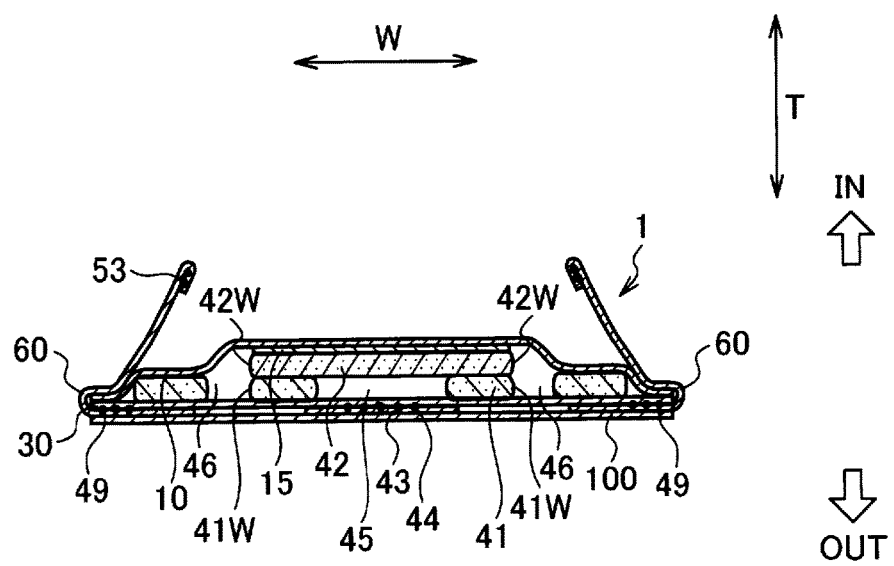

[Fig. 4]
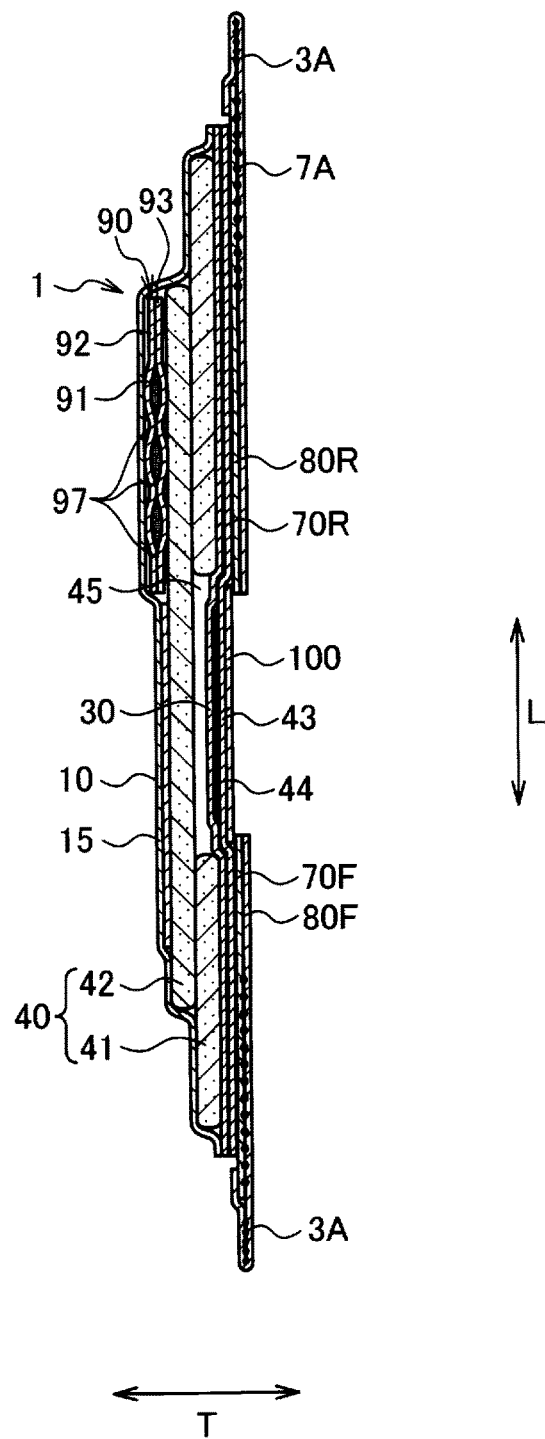

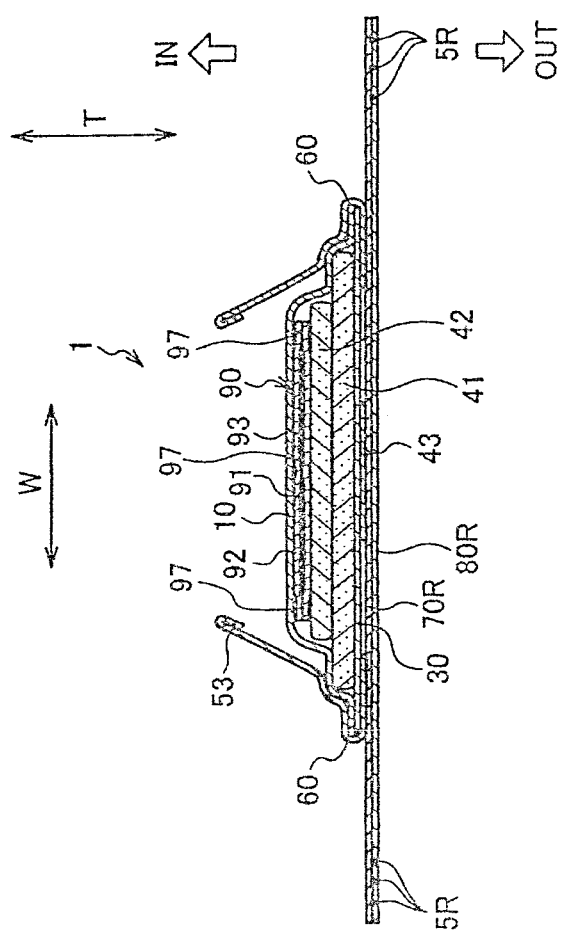
[Fig. 5]

[Fig. 6]
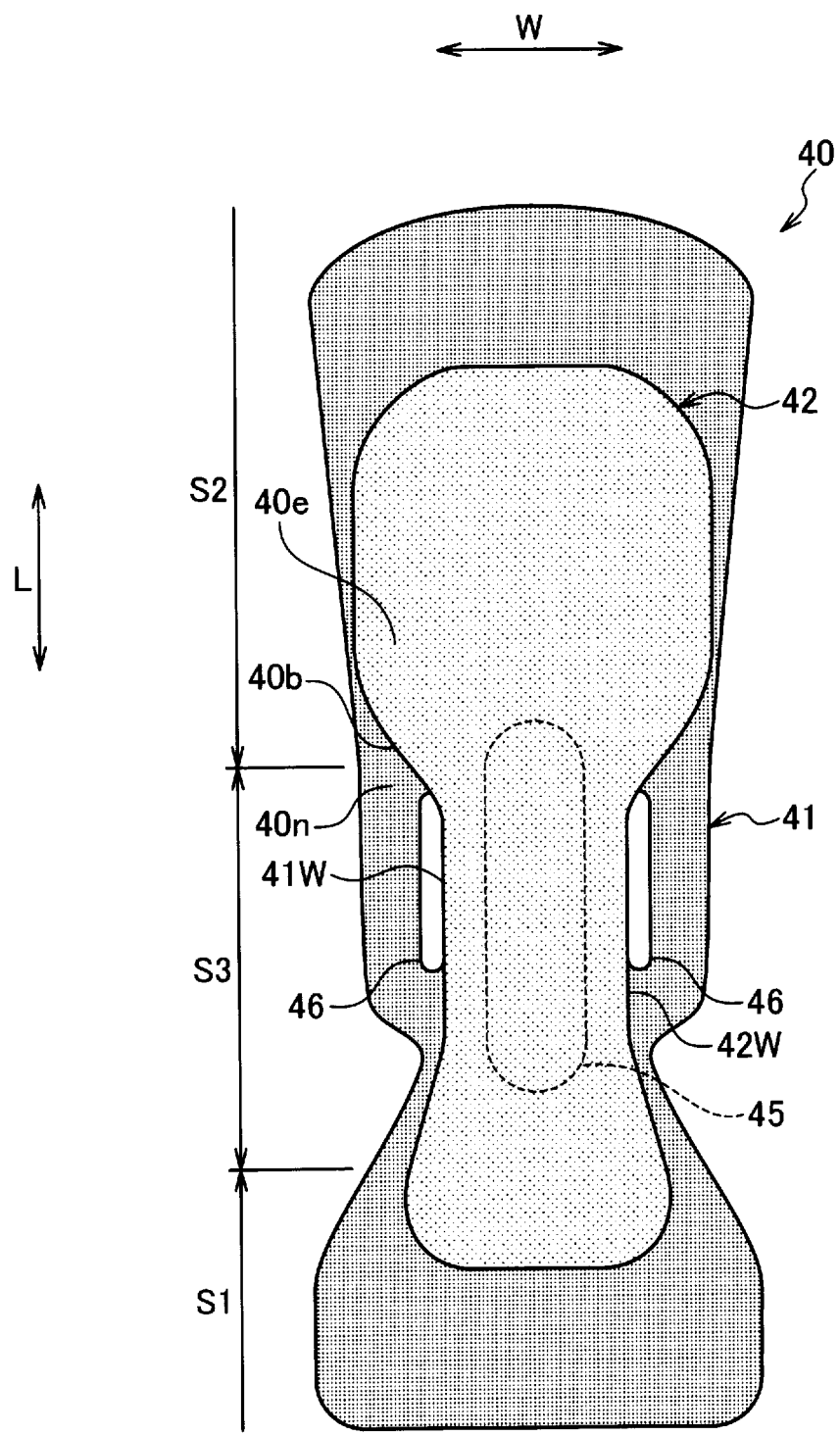

[Fig. 7]
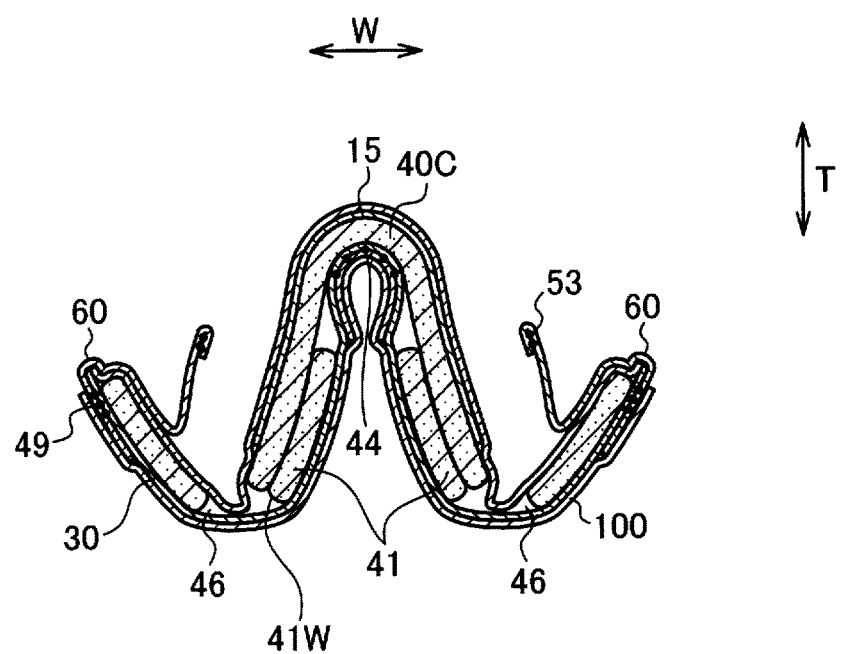

[Fig. 8]
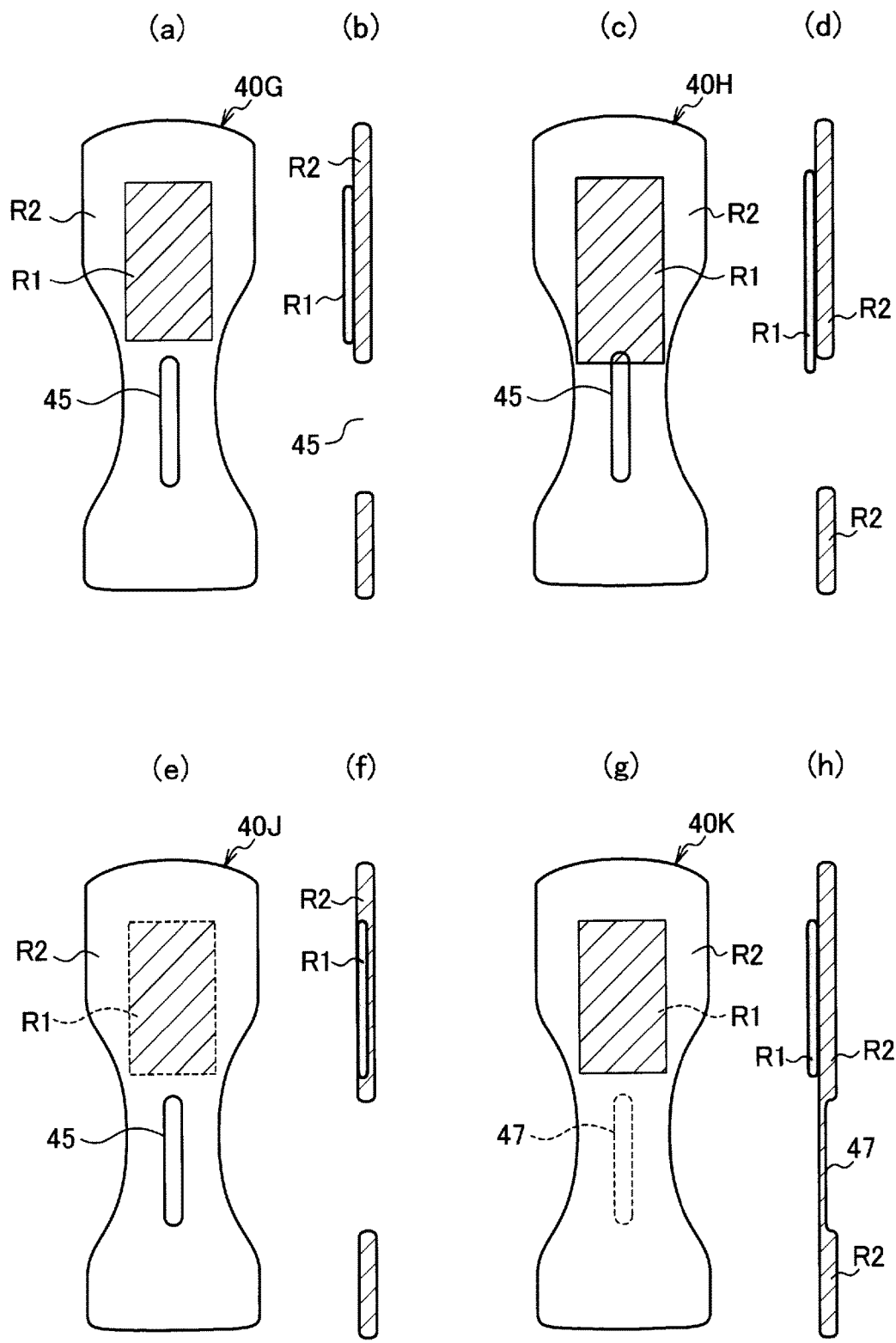

DISPOSABLE WEARING ARTICLE WITH CURVING UNIT

RELATED APPLICATIONS

The present application is a National Phase of International Application Number PCT/JP2012/005617, filed Sep. 5, 2012, and claims priority from Japanese Application Number 2011-195207, filed Sep. 7, 2011.

TECHNICAL FIELD

The present disclosure relates to a disposable wearing article having a curving unit that enables an absorber to be curved.

BACKGROUND ART

Japanese Unexamined Patent Application Publication No. H08-508662 discloses an absorption material provided with a plurality of absorption layers. This absorption material has a storage layer composed of a mixture of a hydrophilic fiber material and scattered particles of an absorption gelling material, and an acquisition layer positioned so as to have liquid communication with the storage layer. The acquisition layer is disposed closer to a surface than the storage layer. The acquisition layer is provided with an acquisition band for spherical absorption of bodily fluids and a distribution band for distributing a liquid, the distribution band being disposed so as to have liquid communication with the acquisition band. The configuration is such that bodily fluids that have been drawn in by the acquisition band are distributed by the distribution band and migrate to the storage layer.

CITATION LIST

Patent Literature

[PTL 1] Japanese Unexamined Patent Application Publication (Translation of PCT Application) No. H08-508662 (FIG. 2 and others)

SUMMARY OF INVENTION

However, the inventor(s) has/have recognized that the above described absorption material might have the following problems.

The absorption material has a smooth shape when seen in plan view, and no structure for being in close contact with the crotch portion when fitted to a wearer is provided; therefore, once fitted, there is the concern that the absorption material might not be placed in close contact with the wearer. When the absorption material is not placed in close contact with the wearer, a bodily fluid sometimes moves down in the skin in a case where the discharge speed of the bodily fluid is comparatively slow or where the wearer is lying on his/her side. When the bodily fluid moves down the skin of the wearer, the bodily fluid sometimes does not reach the acquisition band of the acquisition layer but does reach the distribution band of the acquisition layer. The distribution band of the acquisition layer has less ability to draw in the bodily fluid than does the acquisition band, and there is the concern that the decreased ability to draw in the bodily fluid will cause the absorption performance to deteriorate. Also, because the distribution band of the acquisition layer has less ability to draw in the bodily fluid than does the acquisition band, there is the concern that, in a case where, for example, a large amount of bodily fluid is discharged in a short period of time, then the bodily fluid might spread as far as above the topsheet covering the distribution band.

In view whereof, the present invention addresses the problem of providing a disposable wearing article by which absorption performance can be ensured and, at the same time, any deterioration in absorption performance can be prevented by improving the fit in the proximity of the crotch portion of the wearer.

A disposable wearing article in accordance with some embodiments includes a liquid-permeable topsheet; a backsheet; an absorber disposed between the topsheet and the backsheet, the absorber having a longitudinal direction, a widthwise direction orthogonal to the longitudinal direction, an inner direction for facing a wearer, and an outer direction opposite to the inner direction; a urination region, which is adapted to be in contact with a urination unit of the wearer; a buttocks region, which is disposed rearwardly of the urination region and is adapted to be in contact with buttocks of the wearer; and an absorbent sheet which includes an absorbent polymer sandwiched between liquid-impermeable layers and is provided between the topsheet and the absorber. A curving unit is formed in at least the urination region for causing the absorber to curve convexly in the inner direction. The absorbent sheet is disposed in the buttocks region, but not in the urination region.

A disposable wearing article in accordance with some embodiments includes a liquid-permeable topsheet; a backsheet; an absorber disposed between the topsheet and the backsheet, the absorber having a longitudinal direction, a widthwise direction orthogonal to the longitudinal direction, an inner direction for facing a wearer, and an outer direction opposite to the inner direction; a urination region, which is adapted to be in contact with a urination unit of the wearer; a buttocks region, which is disposed rearwardly of the urination region and is adapted to be in contact with buttocks of the wearer. The absorber has a first region having an absorbent polymer, and a second region where the basis weight of the absorbent polymer is lower than a basis weight in the first region. A curving unit is formed in at least the urination region for causing the absorber to bend convexly in the inner direction. The second region is provided to the absorber in the urination region. The first region is provided to a topsheet side of the absorber in the buttocks region.

BRIEF DESCRIPTION OF DRAWINGS

FIG. 1 is a perspective schematic view of a disposable diaper 1 according to at least one embodiment.

FIG. 2 is an exploded plan view of the disposable diaper 1.

FIG. 3 is a widthwise cross-sectional view of the disposable diaper 1 along the X1-X'1 line shown in FIG. 2.

FIG. 4 is a crosswise cross-sectional view of the disposable diaper 1 along the X2-X'2 line shown in FIG. 2.

FIG. 5 is a widthwise cross-sectional view of the disposable diaper 1 along the X3-X'3 line shown in FIG. 2.

FIG. 6 is a plan view of an absorber according to at least one embodiment.

FIG. 7 is a cross-sectional view along the X1-X'1 line that schematically illustrates the wearing state of the disposable diaper 1 according to at least one embodiment.

FIGS. 8(a), 8(b), 8(c), 8(d), 8(e), 8(f), 8(g) and 8(h) are plan views and sectional views of absorbents of disposable diapers according to various modifications.

DESCRIPTION OF EMBODIMENTS

Next, embodiments of a disposable diaper 1 according to the present disclosure will be described with reference to the drawings. It is to be noted that in the following description of the drawings, same or similar constituent elements are designated by same or similar reference numerals. However, it should be kept in mind that the drawings are schematic representations and are not drawn to scale unless otherwise specified. Moreover, the drawings do not necessarily reflect the actual dimensional relationships and ratios of component. Therefore, specific dimensions or the like should be determined in consideration of the following description. In addition, relations or ratios among such dimensions may be different from one drawing to another.

The disposable wearing article according to at least one embodiment is characterized in that a region where an absorbent polymer for absorbing bodily fluid has a high basis weight is provided to a buttocks region. The basis weight of the absorbent polymer at the region is 168 g/m$^2$, for example.

(1) Overall Schematic Configuration of the Disposable Wearing Article

FIG. 1 is a perspective schematic view of a disposable diaper 1 that configures the disposable wearing article in at least one embodiment. FIG. 2 is an exploded plan view of the disposable diaper 1 according to at least one embodiment. FIG. 3 is a widthwise cross-sectional view of the disposable diaper 1 along the X1-X'1 line shown in FIG. 2. FIG. 4 is a crosswise cross-sectional view of the disposable diaper 1 along the X2-X'2 line shown in FIG. 2. FIG. 5 is a widthwise cross-sectional view of the disposable diaper 1 along the X3-X'3 line shown in FIG. 2. The disposable diaper 1 is a pants-type disposable diaper.

The disposable diaper 1, as illustrated in FIG. 2, has, in the longitudinal direction of disposable diaper 1, a front waistline region S1 corresponding to the front waistline of the wearer, a back waistline region S2 corresponding to the back waistline of the wearer, and a urination region S3 corresponding to the inseam of the wearer, the urination region S3 being a region that is adapted to be in contact with the urination unit of the wearer. The urination region S3 is a region which is closer to the front and includes the center of the absorber in the longitudinal direction; the back waistline region S2 is a region that is farther forward than the center of the absorber in the longitudinal direction, and is disposed farther forward than the urination region S3, thus serving as the buttocks region, which is adapted to be in contact with the buttocks of the wearer.

In the case of a rectangular absorber, in order to make it easier to understand which is the front and back of the absorber, an absorbent sheet is colored or a front and back display is printed on a backing sheet or slipless tape so that the longitudinal direction becomes readily recognizable which is particularly appropriate for a pad-type diaper.

Front waistline edges 4, 4' of the front waistline region S1 are joined to back waistline edges 6, 6' of the back waistline region S2, whereby the disposable diaper 1 is formed into the pants type.

The disposable diaper 1 is provided with the topsheet 10, the absorber 40, a sidesheet 60, a foreside exterior topsheet 70F, an exterior center sheet 100, a foreside exterior backsheet 80F, a backside exterior backsheet 80R, and the like, each of these elements being joined to each other by an adhesive, thermal fusion joining, or the like.

The foreside exterior topsheet 70F, the backside exterior topsheet 70R, the foreside exterior backsheet 80F, the backside exterior backsheet 80R, and the exterior center sheet 100 are sheets configuring an exterior portion of the disposable diaper 1. The absorber 40 configured from cotton-like pulp and highly polymerized water absorbent polymer is provided on the inner side (skin contact surface side) of the foreside exterior topsheet 70F, the backside exterior topsheet 70R, and the exterior center sheet 100.

The topsheet 10 is a sheet that forms the skin contact surface that can be in direct contact with the skin of the wearer. The topsheet 10 is formed by a liquid-permeable sheet, such as a hydrophilic nonwoven cloth and woven cloth, an aperture plastic film, or an aperture hydrophobic nonwoven cloth. The topsheet 10 according to at least one embodiment is formed of a hydrophilic spun bond nonwoven cloth having a basis weight of 23 g/m$^2$ of polypropylene.

An auxiliary sheet 15 is joined with the non-skin contact surface side of the topsheet 10. The auxiliary sheet 15 is disposed between the topsheet 10 and the absorber 40. Providing the auxiliary sheet 15 makes it possible to increase the speed at which the bodily fluid is absorbed, and makes it possible to prevent reversal of the bodily fluid after absorption.

The absorber of the disposable diaper 1 according to at least one embodiment is structured to be in close contact with the crotch portion of the wearer, and therefore preventing reversal of the bodily fluid after absorption makes it possible to improve comfort after excretion. The auxiliary sheet 15 is made of, for example, an air-through nonwoven cloth, a porous film, or the like. The auxiliary sheet 15 of at least one embodiment is formed of 50 g/m$^2$ (hydrophilic) air-through nonwoven cloth.

The absorber 40 is disposed between a composite sheet where the topsheet 10 and the auxiliary sheet 15 are joined, and an absorber backside covering sheet 30 (as a backsheet). The absorber 40 has a longitudinal direction from the front waistline region S1 to the back waistline region S2, and a widthwise direction W perpendicular to the longitudinal direction. The absorber 40 has an inner direction IN towards the wearer wearing the disposable diaper 1 and an outer direction OUT towards the opposite side of the inner direction. The absorber 40 is formed of a mixed powder of ground pulp, highly absorbent polymer, and the like.

The absorber 40 is configured using a first layer 41 disposed closer to the non-skin contact surface with the wearer and a second layer 42 overlapping with the first layer 41 and disposed closer to the skin contact surface of the wearer. The first layer 41 of the absorber 40 has a central aperture 45 formed in the center in the widthwise direction W. A pair of first side slits 46 is formed outboard of the central aperture 45 in the widthwise direction. A more detailed description of the configuration of the absorber 40 shall be provided below. The central aperture and the first side slits function as the curving unit described below, and also function as a body fluid guide unit.

An absorbent sheet 90 is disposed on the skin contact surface side of the absorber in the back waistline region. The absorbent sheet is disposed behind the auxiliary sheet 15. The absorbent sheet is a composite sheet including an absorbent polymer to hold bodily fluid in the back waistline region, thus preventing bodily fluid held by the absorber from returning toward the wearer. A more detailed description of the configuration of the absorbent sheet shall be provided below.

The disposable diaper 1 has a central elastic member 44 disposed so as to overlap on the central aperture 45 in the thickness direction T of the disposable diaper 1.

As a result of the elastic members and slits formed in the absorber 40, the absorber 40 is configured to curve when the disposable diaper 1 is worn. In at least one embodiment, the central elastic member 44 and the central aperture 45 configure a central curving unit, and the first side slits 46 configure a first curving unit.

The sidesheet 60 is provided on both ends of the widthwise direction of the absorber 40 so as to integrally include the topsheet 10 and the absorber backside covering sheet. The sidesheet 60 is formed of a liquid-impermeable nonwoven cloth or the like. The sidesheet 60 according to at least one embodiment is 15 g/m$^2$ polypropylene SMS (spunbond-meltblown-spunbond) nonwoven cloth.

Both the sidesheets overlap at the end in the widthwise direction of the sidesheets 60. The portion where the sidesheets overlap with each other has a leakage-preventing elastic member 53 (see FIG. 3) in a state stretched out along the longitudinal direction. The sidesheet 60 and the leakage-preventing elastic member 53 configure a leakage-preventing wall for preventing side leakage of excretions.

The leakage-preventing wall is provided along the longitudinal direction of the disposable diaper 1, at both ends in the widthwise direction of the absorber 40. The leakage-preventing elastic member 53 is provided as a plurality along the longitudinal direction of the disposable diaper 1 in a state stretched out in the longitudinal direction of the disposable diaper 1, between the sidesheets 60 having been folded together.

The leakage-preventing elastic member 53 according to at least one embodiment uses spandex, extended and fixed in twos at a thickness of 780 dtex and an extension magnitude of 3.0 times on the left and right sides. The sidesheet 60 is fixed to the non-skin contact surface side of the absorber backside covering sheet, and is folded closer to the topsheet than the two ends of the absorber in the widthwise direction. The sidesheet 60 is fixed to the topsheet 10 by being coated with a plurality of 0.1 g/m increments of a hot melt adhesive using a bead coating method.

The exterior top sheet is provided with the foreside exterior topsheet 70F disposed in the front waistline region S1, and with the backside exterior topsheet 70R disposed in the back waistline region S2. In the thickness direction T, the foreside exterior topsheet 70F is disposed between the backside exterior backsheet 80F and the absorber 40. In the thickness direction T, the backside exterior topsheet 70R is disposed between the backside exterior backsheet 80R and the absorber 40. In the longitudinal direction, the exterior center sheet 100 is disposed between the foreside exterior topsheet 70F and the backside exterior topsheet 70R.

The front end of the exterior center sheet 100 is joined with the back end of the foreside exterior topsheet 70F, and the back end of the exterior center sheet 100 is joined with the front end of the backside exterior topsheet 70R. The exterior center sheet 100 is disposed straddling the foreside exterior topsheet 70F and the backside exterior topsheet 70R. The exterior center sheet 100 is joined to the surface side of the exterior topsheet by a hot melt adhesive continuously coated thereon with a slot coater.

The exterior center sheet 100 is constituted of a nonwoven cloth or the like. The exterior topsheet according to at least one embodiment is constituted of an SMS nonwoven cloth having a basis weight of 15 g/m$^2$ of polypropylene. When worn, the exterior center sheet 100 is located further inward (toward the skin contact surface) than the exterior topsheet.

In the front waistline region S1 and the back waistline region S2, the foreside exterior topsheet 70F and the backside exterior topsheet 70R are formed so as to have a width in the widthwise direction W greater than that of the urination region S3. The foreside exterior topsheet 70F and the backside exterior topsheet 70R can be formed by an air-through nonwoven cloth, a spun bond nonwoven cloth, an SMS nonwoven cloth, or a water-resistive film. The exterior topsheet according to at least one embodiment is constituted of an SMS nonwoven having a basis weight of 15 g/m$^2$ of polypropylene.

In the front waistline region S1, the foreside exterior backsheet 80F is provided closer to the non-skin contact surface than the foreside exterior topsheet 70F. In the back waistline region S2, the backside exterior backsheet 80R is provided closer to the non-skin contact surface than the backside exterior topsheet 70R. One end of the foreside exterior backsheet 80F in the longitudinal direction (the backside exterior backsheet 80R) is folded toward the skin contact surface and is provided so as to include an end of the foreside exterior topsheet 70F (the backside exterior topsheet 70R) in the longitudinal direction.

The foreside exterior backsheet 80F and the backside exterior backsheet 80R can be formed by an air-through nonwoven cloth, a spun bond nonwoven cloth, an SMS nonwoven cloth, or water-resistive film, or the like. The foreside exterior backsheet 80F and the backside exterior backsheet 80R according to at least one embodiment are constituted of a spun bond nonwoven cloth having a basis weight of 17 g/m$^2$ of polypropylene.

The absorber backside covering sheet 30 is partially attached to the foreside exterior topsheet 70F, the backside exterior topsheet 70R, and the exterior center sheet 100.

Waist gathers 3 are provided to the front waistline region S1 and to the back waistline region S2. The waist gathers 3 have an elongated waist elastic member 3A of synthetic rubber, for example, that is laid out to expand and contract along the widthwise direction W of the absorber 40. The waist elastic member 3A is joined using an adhesive (for example, a hot melt adhesive) between the foreside exterior topsheet 70F and the foreside exterior backsheet 80F, and between the backside exterior topsheet 70R and the backside exterior backsheet 80R, in an elongated state relative to the widthwise direction W of the disposable diaper 1.

Disposing the waistline elastic member makes it possible to hold the disposable wearing article at the waistline, and makes it possible to prevent the entire disposable wearing article from hanging down. Accordingly, even in a case where bodily fluid is held by the absorbent sheet 90 (described later) and the rear side of the absorber becomes heavy, it is still possible to prevent the absorber from hanging down and possible to suppress the creation of a gap between the absorber 40 and the body of the wearer.

The waist gathers 3 continue from one front waistline edge 4 to the other front waistline edge 4' of the disposable diaper 1 in the front waistline region S1, and also continue from one back waistline edge 6 to the other back waistline edge 6' of the disposable diaper 1 in the back waistline region S2.

Leg gathers 5 are formed in the backside exterior backsheet 80R. The leg gathers 5 are formed to run along the leg portions of the wearer. The leg gathers are formed from a synthetic rubber or other long and narrow leg-holes elastic member disposed so as to stretch. The leg-holes elastic member is constituted of a foreside leg-holes elastic member 5F disposed in the front waistline region S1, and a rear leg-holes elastic member 5R arranged in the back waistline region S2. The leg gathers 5 are provided without crossing the absorber 40.

The leg-holes elastic member functions as a buttocks stretchable member for suppressing the back waistline region S2, serving as a buttocks region, from hanging down due to the absorbent sheet 90 (described below). When bodily fluid is concentrated in the absorbent sheet 90, there is the concern that the back waistline region S2, in which the absorbent sheet 90 is disposed, will fall down. However, disposing the leg-holes elastic member, which is stretchable in the longitudinal direction, outboard of the absorbent sheet in the widthwise direction makes it possible to suppress the back waistline region S2 from hanging down. From such a standpoint, the leg-holes elastic member is disposed, in some embodiments, in the vicinity of the front end of the absorbent sheet 90.

The buttocks stretchable member in some embodiments of the present invention may be configured so as to be stretchable in the longitudinal direction in the state prior to being fitted to the wearer. For example, in the state of having been fitted to the wearer, the longitudinal direction, in the state prior to fitting, of a portion of the absorber 40 disposed on the back waistline region S2 becomes the vertical direction. Accordingly, the buttocks stretchable member is stretchable vertically after having been fitted to the wearer and functions so as to suppress the downward falling of the back waistline region S2.

Of the longitudinal direction and the widthwise direction, the buttocks stretchable member in some embodiments of the present invention may be configured so as to be stretchable in at least the longitudinal direction, or may be configured so as to be stretchable not only in the longitudinal direction but also in the widthwise direction. For example, the buttocks stretchable member may be a stretchable member which is stretchable in an inclined direction relative to the longitudinal direction, and has a component which is stretchable in the widthwise direction and a component which is stretchable in the longitudinal direction. Accordingly, the buttocks stretchable member may be disposed inclining relative to the longitudinal direction in some embodiments, or may be disposed along the longitudinal direction in further embodiments.

The leg-holes elastic member is joined between the foreside exterior topsheet 70F and the foreside exterior backsheet 80F, and between the backside exterior topsheet 70R and the backside exterior backsheet 80R.

The leg-holes elastic member in at least one embodiment is extended and fixed in threes at a thickness of 780 dtex and an extension magnitude of 1.5 to 3.5 times. The leg-holes elastic member is disposed in a state where each portion is given a gradient of magnitude.

The leg-holes elastic member is fixed by a hot melt adhesive pre-coated onto the exterior topsheet. The hot melt adhesive is coated thereon using a spiral sprayer. The amount coated on the leg-holes elastic member is 7 g/m². The position of the vicinity of the end of the exterior topsheet (a position about 5 mm from the end) where there is overlap with at least the leg holes elastic member is coated with the adhesive using a slot coater. Coating the adhesive in this manner makes it possible to prevent the leg-holes elastic member from falling out from the end of the exterior topsheet.

When the adhesive is coated on with a contact-free spiral sprayer, there is the concern that the adhesive in the vicinity of the end of the exterior topsheet will be jut out, and that a manufacturing defect will occur. However, using a contact-type slot coater for the coating makes it possible to prevent the adhesive from jutting out. The amount coated on with the slot coater is 10 g/m².

The central elastic member 44 is provided along the longitudinal direction and is provided at a position of the disposable diaper 1 having overlap with the central aperture 45 in the thickness direction T. The central elastic member 44 is formed so as to be convex in the inner direction IN, i.e., so as to overlap onto the absorber 40 along the longitudinal direction, such that the absorber 40 curves convex toward the wearer. The central elastic member 44 is disposed in an elongated state along the longitudinal direction so as to be stretched in the longitudinal direction in the center in the widthwise direction of the disposable diaper. The central elastic member 44 configures a curving unit stretchable member, and is disposed in the urination region S3.

The central elastic member 44 is provided in an elongated state between an elastic covering sheet 43 and the absorber backside covering sheet 30. The central elastic member 44 is disposed at an extension magnitude of 1.4 to 3.0 times. The central elastic member according to at least one embodiment has a central elastic member located in the center in the widthwise direction, and an auxiliary central elastic member located outboard of the central elastic member in the widthwise direction.

The central elastic member is disposed at an extension magnitude of 1.4 to 3.0. The central elastic member according to at least one embodiment is extended and fixed by threes at a thickness of 620 dtex and an extension magnitude of 2.5 times. The central elastic members have a gap of 5 mm and all have an adhesion length of 120 mm. The central auxiliary elastic member is disposed with less stress than the central elastic member, at a magnitude of 1.2 to 2.5 times. The central auxiliary elastic member according to at least one embodiment is extended and fixed one at a time at a thickness of 620 dtex and an extension magnitude of 1.8 times. A 5-mm gap is opened in the widthwise direction from the two ends of the central elastic member, and it is disposed at 5-mm gaps in the same position in the longitudinal direction as the central elastic member.

The central elastic member 44 is spandex, and is coated with a hot melt adhesive using the V-slot technique. A stretchable nonwoven cloth or the like may be used for the central elastic member 44. The elastic member covering sheet 43 is configured from a nonwoven cloth or other sheet, and, in at least one embodiment, an SMS nonwoven cloth (hydrophobic) having a basis weight of 15 g/m² of polypropylene is used.

Examples of the material of the central elastic member 44 include synthetic rubber such as styrene-butadiene, butadiene, isoprene, and neoprene, natural rubber, EVA, elastic polyolefin, spandex, and foamed polyurethane. In addition, examples of the material of the central elastic member 44 include an elastic sheet such as a stretchable nonwoven cloth formed by mixing and then stretch-processing urethane, polystyrene or other elastomer fiber with stretchable polyolefin, polyester, or other thermoplastic fiber.

A side end elastic member 49 is joined by an adhesive between the absorber backside covering sheet 30 and the sidesheet 60 at both side portions in the widthwise direction of the absorber. The side end elastic member is disposed along the longitudinal direction, and is disposed so as to straddle the urination region S3 and a portion of the back waistline region S2.

Means for fixing the side end elastic member 49 include a hot melt adhesive or the like. The side end elastic member 49 according to at least one embodiment uses spandex and is directly coated with a hot melt adhesive using the V-slot technique. The side end elastic member 49 according to at least one embodiment is extended and fixed in threes on both the left and right sides at a thickness of 780 dtex and an extension magnitude of 2.3 times.

The side end elastic member 49 and the foreside leg-holes elastic member 5F, as well as the side end elastic member 49 and the rear leg-holes elastic member 5R, are disposed substantially in respective series when seen in plan view. Disposing these elements in this manner makes it possible to cause them to stretch so as to surround the leg hole, and has the effects of improving the fit with the leg hole and of preventing displacement or leakage of the diaper.

Note that the extension stress of the elastic members can be measured as described below, for example.

(1) The whole material holding in the elastic member is cut out so as to include the entirety, in the widthwise direction, of the elastic member forming the convex portion. Specifically, in the worn article according to at least one embodiment, the material holding in between the three central elastic members arranged at an interval of 5 mm is cut out at a width of 13 mm and a length of 100 mm in an extended state such that there is no sagging. Similarly, in the extended state, markings are made on the inside at 10 mm from both ends in the longitudinal direction. A tensile tester made by Instron Japan Co., Ltd. (for example, model No. 5564), or Autograph by Shimadzu Corporation (for example, model No. AGS-1kNG) is used for measuring the extension stress.

(2) The test sample of (1) is held between an upper chuck and a lower chuck such that the marking coincides with the inner end of the upper chuck, and the marking on the other side coincides with the inner end of the lower chuck. The length of the test sample between the chucks is 80 mm. Note that when the effective length of the gathers of the elastic members is shorter than 100 mm, the length that is 20 mm shorter than the shortest length in the effective length of the gathers of the elastic members is set as the length of the test sample between the chucks. The initial distance between the chucks is set shorter than the length (natural length) when the test sample is compressed in between, such that the tension of the test sample is not exerted initially. In order to alienate the chucks from each other, the test sample is pulled up and down under a condition of 100 mm/min., and the test sample is extended.

(3) By assuming the length of the test sample between the chucks at the time of extension of the material holding the elastic member without any sagging as 100%, the test sample is extended such that the length of the test sample between the chucks becomes 90%, and the stress during extension of the test sample is measured and set as the extension stress of the elastic member. That is, in the above embodiment, the extension stress when the test sample is extended up to 72 mm, which is 90% of 80 mm—the 100% length of the test sample—is measured.

The thickness of the absorber 40 is measured by inserting the portion to be measured in a thickness measurement gauge in a state where the absorber 40 has been extended to the product length and the product width (that is, a planar state in which no wrinkles are formed). A thickness gauge manufactured by PEACOCK (measurement portion: 5-mm diameter, pressure at the time of measurement: 163 g/c m$^2$) can be used as the measurement device, for example.

As for each member configuring the aforementioned disposable diaper 1, the material described in Japanese Unexamined Patent Publication No. 2006-346439, which is incorporated by reference herein in its entirety, may be used.

(2) Configuration of the Absorbent Sheet

Next, a description of the absorbent sheet 90 disposed on the skin contact surface side of the absorber 40 in the back waistline region S2 shall now be provided. The absorbent sheet 90 is a composite sheet which includes the absorbent polymer 91 sandwiched between at least two liquid-permeable layers, e.g., liquid-permeable sheets 92 and 93. A nonwoven cloth, for example, is used as the liquid-permeable sheets 92 and 93. The absorbent polymer 91 may be sandwiched between three or more liquid-permeable sheets to make the absorbent sheet, or a single liquid-permeable sheet may be folded over to sandwich the absorbent polymer and make the absorbent sheet.

The absorbent polymer 91 is a polymer which absorbs water and is, for example, a highly polymerized absorbent polymer having a three-dimensional network structure in which a water-insoluble polymer has been moderately crosslinked. Such a highly polymerized absorbent polymer absorbs several hundred to a thousand times the volume before the water is absorbed, but is substantially water-insoluble, and water, once absorbed, will be unlikely to be exuded, even when a certain amount of pressure is applied.

Examples of the absorbent polymer 91 include starch-based, acrylic acid-based, or amino-acid based particulate or fibrous polymers. After the absorbent polymer 91 has been sandwiched with the two liquid-permeable sheets 92 and 93, the two liquid-permeable sheets 92 and 93 are joined, thus making the absorbent sheet 90. The particle diameter of the absorbent polymer 91, in some embodiments, is not finer than the gaps between fibers in the liquid-permeable sheets 92 and 93, in order to prevent the absorbent polymer 91 from creeping through after the absorbent polymer 91 has been sandwiched with the two liquid-permeable sheets 92 and 93.

The liquid-permeable sheets 92 and 93 can be formed from, for example, spun bond nonwoven cloth, point-bond nonwoven cloth, air-through nonwoven cloth, SMS nonwoven cloth, or the like. The liquid-permeable sheets 92 and 93 are permeable to urine, and therefore a hydrophilization treatment is performed in some embodiments. In at least one embodiment, a 25 g/m$^2$ air-through nonwoven cloth to which a hydrophilization treatment has been performed is used as the liquid-permeable sheets 92 and 93.

The surface of the liquid-permeable sheets 92 and 93 where the absorbent polymer 91 is sandwiched is provided with a plurality of adhesive portions (not shown) extending in the longitudinal direction and lined up in the widthwise direction. The adhesive portions may also be provided to the surface of one of the liquid-permeable sheets 92 and 93 where the absorbent polymer 91 is sandwiched. The adhesive portions are formed by, for example, coating a hot melt adhesive in streaks.

The absorbent polymer 91 is thereby fixed to the liquid-permeable sheets 92 and 93. The plurality of adhesive portions extend in the longitudinal direction and are lined up in the widthwise direction, i.e., the adhesive portions are in streaks in order to provide regions where no adhesive portion is present since permeability to urine is prone to be decreased at the adhesive portions. Accordingly, provided that the coating method be able to provide regions where no adhesive portion is present, i.e., provided that the coating method be able to intermittently dispose the adhesive portions, there is no limitation to the streaking coating method, and an omega coating method or other contact-free coating method may be used.

Because the adhesive portions are provided intermittently to an absorbent polymer containing region 96 (described below), it is possible to prevent the absorbent polymer 91 from being shifted within the absorbent polymer containing region 96. The distance between the adhesive portions between mutually adjacent adhesive portions of the adhesive portions provided to the liquid-permeable sheet 93 on the absorber 40 side is less than the distance between the adhesive portions of the adhesive portions provided to the liquid-permeable sheet 92 on the topsheet 10 side. The absorbent polymer is thereby evenly fixed to the liquid-permeable sheet 93 on the absorber 40 side.

Providing the streaked adhesive portions colored to be blue or another color to the liquid-permeable sheets 92 and 93 improves the outer appearance of the disposable diaper 1, because the disposable diaper 1 is given a pattern of stripes in blue or another color. The adhesive portions may also be provided to only the surface(s) sandwiching the absorbent polymer in the liquid-permeable sheet 93 on the absorber 40 side. Providing the adhesive portions to the liquid-permeable sheet 92 and/or 93 makes it possible to suppress movement of the absorbent polymer throughout the absorbent sheet 90 before the absorbent polymer swells. In some embodiments, the absorbent sheet 90 is disposed in a partial region of at least the back waistline region S2.

Disposing the absorbent polymer in this concentrated manner in the back waistline region S2 improves the absorption performance in the back waistline region S2 and, in particular, makes it possible to mitigate leakage from the back waistline region, which often occurs in cases of sitting and sleeping postures.

In the absorbent sheet 90, the absorbent polymer is disposed divided into a plurality of absorbent polymer containing regions 96, and a region 97 where the absorbent polymer is not disposed (hereinafter, "absorbent polymer non-containing region") is provided between each pair of the adjacent absorbent polymer containing regions 96. FIG. 2 shows the absorbent polymer containing regions 96 with diagonal lines.

Interchangingly disposing the polymer containing regions and polymer non-containing regions causes urine to flow through the absorbent polymer non-containing regions 97 and be absorbed by the absorber 40 even in a case where the absorbent polymer of the absorbent polymer containing regions 96 has absorbed urine and becomes swollen, thus becoming unable to further absorb urine. There is no need to provide the absorbent polymer non-containing regions to the absorbent sheet for an absorbent article that will not be continuously used until the absorbent polymer has become swollen.

The shape of the absorbent polymer containing regions 96 in the planar direction is convex in the direction from the front waistline region S1 to the back waistline region S2 in the longitudinal direction of the disposable diaper 1, and is substantially V-shaped extending in the widthwise direction of the disposable diaper 1. Specifically, the shape of the absorbent polymer containing regions 96 in the planar direction is substantially V-shaped where the vortex faces the direction from the front waistline region S1 to the back waistline region S2 in the longitudinal direction of the disposable diaper 1. The absorbent polymer containing region 96 most separated from the front waistline region S1 has a shape formed by cutting a substantially V-shape or substantially arcuate shape at the center in the widthwise direction in to form two separate regions. The substantially V-shape of the absorbent polymer containing region 96 is a shape that runs along the buttocks portion of the wearer, and therefore the absorbent polymer containing region 96 is fitted to the buttocks portion of the wearer and there are less likely to occur a gap between the wearer and the disposable diaper 1. Provided that the absorbent polymer non-containing regions, the shape of the absorbent polymer containing regions is not limited to being substantially V-shaped. For example, the shape of the absorbent polymer containing regions may be arcuate, circular, rectangular, triangular, or the like.

As described above, after the absorbent polymer has been sandwiched with the two liquid-permeable sheets 92 and 93, the two liquid-permeable sheets 92 and 93 are joined, whereby the absorbent sheet 90 is made. The regions where the absorbent polymer has been sandwiched between the two liquid-permeable sheets 92 and 93 are the absorbent polymer containing regions 96, and the regions where the two liquid-permeable sheets 92 and 93 are joined together without the absorbent polymer having been sandwiched between the two liquid-permeable sheets 92 and 93 are the absorbent polymer non-containing region 97.

The mutual joining of the two liquid-permeable sheets 92 and 93 has a strength able to withstand the expansion force caused by the swelling of the absorbent polymer. In some cases, when, for example, the swelling of the absorbent polymer causes the two liquid-permeable sheets 92 and 93 to peel away from each other, a gap is created between the two liquid-permeable sheets, into which gap the absorbent polymer enters, thus eliminating the absorbent polymer non-containing region 97. For joining the liquid-permeable sheets 92 and 93 to each other, a heat seal, sonic seal, adhesive, or the like can be used.

In a case where a heat seal is used to join the liquid-permeable sheets 92 and 93 to each other, a greater constancy of the line pressure of the heat seal in the widthwise direction corresponds to an overall more even sealing strength. Therefore, in some embodiments, the line pressure of the heat seal in the widthwise direction is constant. In order to even out the line pressure of the heat seal in the widthwise direction, the total length of the sealed region in the widthwise direction is kept constant. For example, as described above, giving the absorbent polymer containing regions 96 a substantially V-shape or substantially arcuate shape and lining them up in a row in the longitudinal direction makes it possible to keep the total length of the absorbent polymer non-containing regions 97 in the widthwise direction substantially constant. In a case where an adhesive is used to join the liquid-permeable sheets 92 and 93 to each other, because the liquid-permeable sheets 92 and 93 are in a wet state when the absorbent polymer has swollen, the adhesive, in some embodiments, is of a type which exhibits strength even when wet.

Because the absorbent polymer swells upon absorbing urine, the absorbent polymer in the absorbent polymer containing regions 96 is configured to have sufficient volume between the two liquid-permeable sheets 92 and 93 so as to allow the absorbent polymer to expand adequately. When the absorbent polymer is too densely packed in between the two liquid-permeable sheets 92 and 93, the absorbent polymer is unable to swell completely, and in some cases it is not possible to fully make use of the absorption performance of the absorbent polymer.

When the number of the absorbent polymer containing regions 96 in the absorbent sheet 90 is increased, the surface area of the absorbent polymer non-containing regions 97 is increased, but the total volume of the absorbent polymer in the absorbent sheet 90 is decreased, and so the amount of urine which can be absorbed by the absorbent sheet 90 is decreased. On the other hand, when the number of the absorbent polymer containing regions 96 in the absorbent sheet 90 is reduced, the total volume of the absorbent polymer in the absorbent sheet 90 is increased and the amount of urine which can be absorbed by the absorbent sheet 90 is increased, but the surface area of the absorbent polymer non-containing regions 97 is decreased, and in some cases, after the absorbent polymer has swollen, urine will be unlikely to further permeate through the absorbent sheet 90 to be absorbed into the absorber 40

In some embodiments, consideration is given to balancing the amount of urine with the urine permeability of absorbent sheet 90 after the absorbent polymer has swollen, and further consideration is given to the type of absorbent polymer and the volume after swelling occurring from the amount inputted, when selecting the number of the absorbent polymer containing regions 96. For example, in a case where the absorbent sheet is sized to 180 mm times 130 mm, disposing 2 g of an absorbent polymer which absorbs 60 g physiological saline per 1 g into five separate absorbent polymer containing regions makes it possible to obtain an absorbent sheet having a favorable balance between urine absorption performance and urine permeability after the absorbent polymer has swollen.

The absorbent sheet 90 may be disposed on the non-skin surface side of the absorber 40, but is preferably disposed on the skin surface side. In a case where the wearer is in a sitting position or sleeping posture, the urine absorbed into the absorber 40 in the region of the back waistline region S2 oozes out due to the application of pressure from body weight (body pressure) onto the absorber 40, but the oozed urine is less prone to reach the skin of the wearer due to the absorbent sheet 90. Because the absorbent sheet 90 is substantially configured from absorbent polymer, urine will essentially not ooze out even in a case where body pressure is applied. Accordingly, even after urine has been excreted, the skin feels clean, and it is possible to suppress irritation of the skin of the wearer due to the excreted urine.

The uplifting effect of the leg-holes elastic member causes such a configuration that the absorber will not be separated from the skin even in a case in which the absorbent sheet 90 absorbs bodily fluid and becomes heavy. Accordingly, it is possible to prevent the creation of a gap between the absorber and the skin, in particular, to reduce the occurrence of leakage caused by running along the skin. In a case where the absorber is configured so as not to be separated from the skin, irritation of the skin is particularly prone to occur when bodily fluid oozing out from the absorber 40 is likely to reach the skin of the wearer. Accordingly, the absorbent sheet 90 is disposed, in some embodiments, on the skin surface side of the absorber 40.

(3) Structure of the Absorber

FIG. 6 is a plan view of the absorber 40. As illustrated in FIG. 6, the absorber 40 has a first layer 41, and a second layer 42 on top of the first layer 41. The first layer 41 is positioned at the non-skin contact surface side of the wearer, and the second layer 42 is positioned at the skin contact surface side of the wearer.

The first layer 41 and the second layer 42 are configured by cotton-like pulp and highly polymerized absorbent polymer (SAP). The absorber 40 can be formed by mixing, for example, 0 to 500 $g/m^2$ pulp and 0 to 500 $g/m^2$ SAP.

The first layer 41 according to at least one embodiment is formed from a mixture of 280 $g/m^2$ pulp and 170 $g/m^2$ SAP, and has a thickness of about 3.1 mm. The second layer 42 according to at least one embodiment is formed from a mixture of 260 $g/m^2$ pulp and 160 $g/m^2$ SAP, and has a thickness of about 2.9 mm. Accordingly, the thickness of the absorber 40 is 6.0 mm.

In the first layer 41, the central aperture 45 and a pair of first side slits 46 are formed. The central aperture 45 is formed in the central portion in the widthwise direction W. The central aperture 45 and the first side slits 46 have an elongated shape extending along the longitudinal direction. The central aperture 45 and the first side slits 46 are formed extending in the longitudinal direction in the urination region S3, and function as a body fluid guide unit for guiding fluid absorbed by the absorber 40 of the urination region S3 to the absorbent sheet 90 of the back waistline region S2.

The rear end of the central aperture 45 may be disposed so as to be over the absorbent sheet 90, or may be disposed so as not to overlap but rather adjacent to the absorbent sheet. The absorbent sheet may also be disposed so as to be present on the rear-facing extended line of the central aperture.

Thus disposing the central aperture and the absorbent sheet facilitates bending of the central portion of the absorber toward the skin of the wearer. Bodily fluid that has been drawn in by the absorber via the central aperture 45 and the first side slits 46 can be guided unencumbered to the back waistline region S2 via the central aperture and the like. Directing bodily fluid to the absorbent sheet 90 disposed in the back waistline region S2 makes it possible to concentrate the bodily fluid in the portion having high absorption performance.

Because the central curving unit is formed in the urination region, the urination region is in close contact with the wearer, and bodily fluid can be drawn in by the absorber disposed in the urination region. The absorbed bodily fluid can be held by the absorbent polymer disposed in the absorbent sheet of the back waistline region.

Accordingly, the urination region functions as an indrawing region for drawing in the bodily fluid, and the back waistline region functions as a holding region for holding the bodily fluid, and each function can be exerted. Accordingly, any deterioration in absorption performance can be prevented.

Consequently, absorption performance can be effectively used and the absorption performance of the entire absorbent article can be improved. When the excreted urine is concentratedly held in the crotch portion, the absorber swells in the crotch portion, it becomes more difficult to close the legs, greater discomfort occurs, and it becomes more difficult to walk. However, directing the urine to, and concentratedly holding the urine in, the distally positioned absorbent sheet separated from the urination region makes it possible to improve absorption efficiency and reduce leakage even while reducing the discomfort caused by the swelling of the absorbent polymer after urine absorption in the crotch portion and caused by an increase in the thickness of the absorber.

A distance of about 10 mm in plan view exists between the absorbent polymer containing region 96 and the central aperture 45. The region between the absorbent polymer containing region 96 and the rear end of the central aperture 45 is termed an intermediate region 110. The intermediate region 110 is configured to be able spread bodily fluid even in a case where urine is repeatedly excreted, in order to concentrate the bodily fluid in the absorbent polymer containing region 96.

Accordingly, even in a case where urine is repeatedly excreted, the intermediate region 110 is configured to be able to spread bodily fluid. Accordingly, the weight ratio of the absorbent polymer in the intermediate region 110 is 0 to 50% in some embodiments, or 20 to 40% in at least one embodiment. The intermediate region of the absorber according to at least one embodiment is a region where the first layer and the second layer overlap, and the weight ratio of the absorbent polymer of this overlapping region is 35%.

The absorber of the urination region S3 serves as an acquisition region for drawing in bodily fluid, and is therefore configured to be able to acquire bodily fluid even in a case where urine is repeatedly excreted. Accordingly, the weight ratio of the absorbent polymer of the absorber in the urination region is 0 to 50% in some embodiments, or 10 to 35% in at least one embodiment. The absorber of the urination region according to at least one embodiment has a side closer to skin contact surface than the central aperture 45, this side being configured from only the second layer, and the weight ratio of the absorbent polymer is 31%.

Further, the holding region of the absorber on the skin surface side of the back waistline region S2, the holding region holding the bodily fluid, is configured to be able to hold large amounts of bodily fluid and is configured such that essentially no bodily fluid oozes out even in a case where body pressure is applied. Accordingly, the weight ratio of the absorbent polymer of the absorber in the holding region is at least 50% in some embodiments.

Note that the holding region in at least one embodiment is a region where the absorbent sheet 90 is located, and is a region where the density of the absorbent polymer is high. The urination region S3 encompasses the entire thickness direction of the absorber 40. The intermediate region 110 encompasses the entire thickness direction of the absorbent sheet 90. The holding region encompasses the region of the disposable diaper 1 on the skin surface side in the thickness direction.

The weight ratio of the absorbent polymer in the holding region can be measured, for example, by the following method. The absorbent sheet is taken out from the product and the absorbent polymer is separated from the two liquid-permeable sheets 92 and 93. When the total weight of the two liquid-permeable sheets 92 and 93 is taken as a (g) and the weight of the absorbent polymer is taken as b (g), the calculation can be made as follows: absorbent polymer weight ratio (%)=polymer weight (b)/(polymer weight (a) plus liquid-permeable sheet total weight (b)) times 100.

In the configuration where the absorbent sheet members are adhered together by a hot melt adhesive, the aforesaid weight serves as a ratio that includes the hot melt adhesive, but the extremely small value thereof compared to the weight of the absorbent polymer or to the liquid-permeable sheet means that it may be ignored.

The curving unit according to at least one embodiment is configured from a slit or other opening formed in the absorber, but there is no limitation to this configuration. For example, the curving unit may be configured from a low basis weight region having a lower basis weight than the basis weight of a surrounding region that surrounds the low basis weight region, or may be configured from a compressing portion where the absorber has been compressed in the thickness direction.

The low basis weight region in some embodiments of the present invention is a region having a basis weight ratio of at most 50% relative to the average basis weight of the absorption layer configuring the surrounding region. The basis weight can be measured by, for example, the following method. Firstly, markings are made on the topsheet at the dimensions of 10-mm width and 50-mm length in the region serving as the product target, and the absorber is taken out sheet member by sheet member in these dimensions to measure the initial weight. This weight is taken as being A (g).

Next, the sheet members cut out together (the topsheet, the auxiliary sheet, the backside covering sheet, and the like) are washed with toluene or another organic solvent and dried, after which the weight is measured, thus determining the total weight of the sheet members. This weight is taken as being B (g).

The basis weight of the absorber is calculated from "(A−B)/Sampling size" with the initial weight (A) and the weight (B) of sheet members. Specifically, the basis weight of at least one embodiment can be calculated from (A−B)/ (10 times 50/1000/1000) (g/m$^2$). The above-noted weight is the weight including hot melt adhesive, but the adhesive weighs much less than the absorber, etc., so that the weight of adhesive may be ignored.

A basis weight ratio is calculated in accordance with the basis weight of the absorber found in the above-noted method.

Basis Weight Ratio=(Basis Weight of Absorber at Low Basis Weight Region)/(Basis Weight of Absorber at Surrounding Region)times 100

The low basis weight region is the region having the basis weight ratio below 50%.

In other words, the region which meets the following condition is identified as the low basis weight region.

(Basis weight of the absorber in the low basis weight region)/(Basis weight of the peripheral absorber)times 100=50(%) or (Basis weight of the absorber in the low basis weight region)/ (Basis weight of the peripheral absorber)times 100<50(%).

In a case where the low basis weight region is at a point where there is no overlap with the other absorption layers (for example, a region formed in the first layer 41, and which is not covered with the second layer 42), the above described method is used to determine the basis weight of the absorption layer of the low basis weight region serving as the target and to determine the basis weight of the surrounding region of the relevant absorption layer.

In a case where the low basis weight region is at a point where there is an overlap with the other absorption layers (for example, a region formed in the first layer 41, and which is covered with the second layer 42), it is difficult to measure the basis weight of the low basis weight region of a single absorption layer, and therefore a basis weight X1 of the portion of the targeted low basis weight region where the absorption layers overlap is determined, a low basis weight X2 of the absorber in the overlapping portion of the surrounding region is then determined, and a basis weight X3 of the portion of the lone layer where there is no overlap is determined, whereby the basis weight of the low basis weight region is measured.

Furthermore, in this case, when (1) the absorption layer having the low basis weight region is the single layer mentioned above, the low basis weight region can be expressed by (X1−X2 plus X3)/X3 times 100=50(%) or (X1−X2 plus X3)/X3 times 100<50(%).

On the other hand, when (2) the absorption layer having the low basis weight region is not the single layer mentioned above, the low basis weight region can be expressed by (X1−X3)/(X2−X3) times 100=50(%) or (X1−X3)/(X2−X3) times 100<50(%).

Specifically, depending on the structure of the low basis weight region, the basis weight can be found by the aforementioned three methods.

Forming the central aperture 45 makes it possible to facilitate convex bending in the inner direction IN, which is the wearer side, of the central portion 40C. The first side slits 46 are formed outboard of the central aperture 45 in the widthwise direction. The first side slits 46 have an elongated shape extending along the longitudinal direction. The pair of first side slits 46 are formed on the absorber 40 along the longitudinal direction convexly in the outer direction OUT, that is, such that the absorber 40 bends convexly inverse to the central aperture 45.

The second layer 42 is a substantially hourglass shape. The configuration can be such that the second layer straddles the interface between the back waistline region S2 and the urination region S3, and has a portion serving as boundaries 40b between the overlapping portion 40e and non-overlapping portion 40n, in the inwardly facing direction heading toward the urination region side when seen in the longitudinal direction. The overlapping portion 40e is an area where the first layer 41 and the second layer 42 are laminated. The overlapping portion has higher bending rigidity than the non-overlapping portion, and therefore can be configured such that the deformation bending in the outer direction OUT, the bending being caused by the first side slits in the urination region, is not transmitted farther rearwardly than the portion serving as the boundary between the overlapping portion and non-overlapping portion relative to the first layer.

In some embodiments, the width of the absorber is 120 to 250 mm in the front waistline region S1 and the back waistline region S2, and 120 to 250 mm in the urination region S3.

The length of the central aperture 45 in the longitudinal direction is longer than the length of the first side slits 46 in the longitudinal direction. In at least one embodiment, the width of the central aperture is 40 mm, and the width of the first side slits 46 is 10 mm each.

In the urination region S3, an outer end 42W of the second layer 42 in the widthwise direction has overlap with an inner end 41W of the first side slit 46 of the first layer, and is disposed along the longitudinal direction. Outboard of the outer end 42W in the widthwise direction, the absorber 40 is configured from the first layer 41 only, and inboard of the outer end 42W in the widthwise direction, the absorber 40 is configured from the first layer 41 and the second layer 42, excluding the portion where the central aperture 45 has been formed. Accordingly, the absorber 40 changes in rigidity and thickness at a boundary formed by the inner end 41W of the first layer 41 and the outer end 42W of the second layer 42. In at least one embodiment, the absorber bends at a boundary formed by the outer end 42W of the second layer where the rigidity and other properties change.

Causing the topsheet 10 and the absorber backside covering sheet 30 to be joined together and fixed at the central aperture 45 makes it possible for the absorber to bend without being shapeless.

(3) Changes in the Shape of the Absorber

FIG. 7 is a cross-sectional view (with reference to the X1-X'1 line of FIG. 1) that schematically illustrates the wearing state of the disposable diaper 1. When the disposable diaper 1 is worn, the urination region S3 of the absorber comes up against the crotch of the wearer. Due to the legs and the like of the wearer, force is applied on the absorber inwardly in the widthwise direction. The absorber 40 bends such that the first side slits 46 as well as the central elastic member 44 and the central aperture 45 are reference points, and the cross-sectional shape of the disposable diaper 1 along the widthwise direction W is deformed in a wavelike manner. Accordingly, the urination region S3 of the absorber 40 enters a regularly folded state.

The top surface of the absorber 40, which becomes convex in the inner direction IN due to the central elastic member 44, comes into contact with the crotch portion of the wearer. The portion where the convex portion, caused by the central curving unit, is formed is configured from only the second layer 42, and is comparatively thinner. On the other hand, the first layer 41 and the second layer 42 overlap between the convex portion caused by the central curving unit and the convex portion caused by the first curving unit, this overlap being comparatively thicker and more rigid. The more rigid portion between the central curving unit and the first curving unit makes it possible to support the convex portion caused by the central curving unit, and makes it possible to enhance the stability of the convex shape caused by the central curving unit.

The configuration may also be such that a central groove or slit extending in the longitudinal direction is provided to the central portion of the central curving unit. The configuration can be such that providing the central groove or slit extending in the longitudinal direction to the central portion of the central curving unit makes it possible to provide a concave portion, which is concave toward the non-skin contact surface, to the central portion in the widthwise direction of the central curving unit, which becomes convex toward the skin contact surface. For example, forming a slit at a position facing the central aperture of the second layer makes it possible to configure such that the topsheet in the relevant portion is deformed so as to be toward the backsheet and bends convexly in the outer direction, because the absorber is not disposed at the portion where the slit has been formed.

When the wearer closes both legs, with respect to the cross-sectional shape of the disposable diaper 1, the absorber is folded over at the central curving unit and the first curving unit and is compactly disposed below the crotch portion in a state of close mutual contact.

At such a time, the central curving unit formed by the central elastic member 44 and the central aperture 45 is positioned so as to be in contact with the crotch portion of the wearer. On the other hand, the first curving unit formed by the first side slits 46 is convex toward the non-skin contact surface, and is positioned so as not to be in contact with the excretion portion of the wearer.

Because the absorber is in close contact at the crotch portion of the wearer, leakage of the bodily fluid can be prevented even in a case where urine slowly is excreted, which would run along the skin. In the folded state, a concavity extending in the longitudinal direction is formed at the curving unit of the portion of the absorber separated from the skin, and therefore the bodily fluid can be spread outward in the longitudinal direction and side leakage can be prevented.

Because the folding has, as reference points, the central aperture 45 and first side slits 46 formed in the absorber, the absorber 40 is more readily bent even in a case where the absorber 40 has absorbed liquid and has swollen, compared to a case where the thin portion of the absorber 40 is formed and serves as the convex portion. The cross-sectional shape when the disposable diaper 1 is worn and the absorber 40 is deformed is a tapered shape which narrows from the non-skin contact surface side to the skin contact surface side. Accordingly, the disposable diaper 1 can be readily fitted into the gap in the crotch portion of the wearer, and is less prone to cause discomfort.

The convex portion formed by the central curve unit is configured from only the second layer 42, and is thinner than the portion configured from the stacking of the first layer 41 and the second layer 42. In other words, due to a thin and high structure, the convex portion formed by the central curving unit can be easily inserted in the thin gap of the crotch portion, and easily comes in close contact with the excretion portion. Accordingly, because there is close contact between the excretion portion and the absorber, excreted urine can be absorbed rapidly. Because the folding is such that the absorber is thin in the portion close to the skin of the crotch portion of the wearer and is thicker at the portion farther from the skin, fitting can be done without discomfort.

The structure that is more readily entered into the thin gap in the crotch portion of the body makes it possible to reduce the distance between the central aperture 45 and the urination unit. Reducing the distance between the central aperture 45 and the urination unit makes it possible to spread excreted urine in the longitudinal direction, due to the central aperture 45, and guide the urine to the absorbent sheet 90 of the back waistline region S2. Unencumbered guidance of bodily fluid to the absorbent sheet 90 makes it possible to concentrate the bodily fluid at the portion having high absorption performance and makes it possible to more efficiently make use of the absorption performance, whereby absorption properties can be further enhanced.

With respect to a method for producing the absorbent article thus configured, the absorbent article can be produced by a method comprising, for example, a step for forming the first layer of the absorber, a step for forming the second layer of the absorber, a step for conjoining the first layer and the second layer, and a step for using a conveyor belt or the like to convey the absorber and the like and, during the process of conveyance, joining the absorbent sheet, the topsheet, and other sheet materials. Production involving other steps is also possible.

In a case where an aperture and side slits are provided to both the first layer and the second layer, sometimes positional deviation when the first layer and the second layer are overlapped may occur. When positional deviation occurs in, for example, the widthwise direction, the width of the pair of side slits disposed on the left and right sides is narrowed, regular deformation becomes impossible, and the absorber has a left-right imbalance, having an adverse effect on absorption and on the fitting sensation. Providing the aperture or slide slits to either one of the first layer or second layer, however, makes it possible to prevent positional deviation of the side slits and the like.

(Disposable Diaper According to Modifications)

A description of the configurations of absorbers of disposable diapers according to modifications shall next be provided, with reference to the accompanying drawings. Aspects of the configuration which are similar to the above described embodiments are given like reference numerals, and a description thereof will be omitted.

FIGS. 8(*a*) and 8(*b*) illustrate an absorber according to a first modification. FIG. 8(*a*) is a plan view, and FIG. 8(*b*) is a cross-sectional view of a cross-section along the longitudinal direction in the center of the absorber in the widthwise direction.

An absorber 40G according to the first modification is configured from a substantially hourglass shaped layer. The absorber 40G has a first region R1 having an absorbent polymer, and a second region R2 having an absorbent polymer at a lower basis weight than that of the first region R1. FIG. 8 illustrates the first region with diagonal lines. The region surrounding the first region in the absorber serves as the second region. The first region is configured by the intermittent disposition of the absorbent polymer, and is disposed on the skin contact surface side of the back waistline region S2 that is adapted to be in contact with the buttocks portion. For example, the first region R1 is defined by an absorbent sheet, such as the absorbent sheet 90, disposed on the skin contact surface side of the back waistline region S2

The second region may be configured to have a lower basis weight of the absorbent polymer than the first region, or may be a region which does not have the absorbent polymer (the basis weight of the absorbent polymer is 0 g/m$^2$).

FIGS. 8(*c*) and 8(*d*) illustrate an absorber 40H according to a second modification. FIG. 8(*c*) is a plan view, and FIG. 8(*d*) is a cross-sectional view of a cross-section along the longitudinal direction in the center of the absorber in the widthwise direction.

The absorber 40H according to the second modification is configured from a substantially hourglass shaped layer. The first region R1 is configured by the disposition of a highly absorbent core, which is a high basis weight region where the absorbent polymer has a higher basis weight than the surrounding region of the absorber, and is disposed on the skin contact surface side of the back waistline region S2 to be in contact with the buttocks portion. For example, the first region R1 is defined by an absorbent sheet, such as the absorbent sheet 90, disposed on the skin contact surface side of the back waistline region S2.

The rear end of the central aperture 45 of the absorber overlaps with the first region R1 in the thickness direction. Such disposition with overlap between the body fluid guide unit and the first region makes it possible to guide bodily fluid that has been absorbed in the urination region S3 directly to the first region. Accordingly, the bodily fluid can rapidly and reliably migrate to the first region, and the efficiency which with the absorbent polymer disposed in the first region is used can be improved.

Because the first region is disposed on the skin contact surface side of the central aperture of the absorber, bodily fluid that is guided by the central aperture is absorbed from the non-skin surface side of the first region. Accordingly, the bodily fluid finds it difficult to touch the skin, making it possible to reduce a wet sensation.

FIGS. 8(*e*) and 8(*f*) illustrate an absorber 40J according to a third modification. FIG. 8(*e*) is a plan view, and FIG. 8(*f*) is a cross-sectional view of a cross-section along the longitudinal direction in the center of the absorber in the widthwise direction.

The absorber 40J according to the third modification is configured from a substantially hourglass layer. A first region R1 is formed by giving a higher basis weight of the absorbent polymer to one portion of the absorber, and is disposed in the back waistline region S2 to be in contact with the buttocks portion.

In the configuration where, as in the third modification, the first region is integrated with the absorber, the weight ratio of the absorbent polymer can be measured by, for example, the following method.

The absorber is divided into the absorber of the skin contact surface side and the absorber of the non-skin contact surface side in the thickness direction. With respect to the absorber of the skin contact surface side, a sieve or the like is used to separate the polymer and the pulp fibers, and the weights of each of the polymer weight C (g) and the pulp fiber weight D (g) are measured. Any of various means can be used for the means for separating, provided that both can be substantially entirely separated. For example, by utilizing a difference in particle size, a fine mesh may be used for the sieve separation, or the difference in weight may be used, where the sample is placed under an air flow such that only the pulp is scattered and the weight before and after scattering is measured.

The calculation can be performed such that the absorbent polymer weight ratio (%)=polymer weight (C)/(polymer weight (C)+pulp fiber weight (D)) times 100.

Additionally, the absorber shown in FIGS. 8 (e) and 8 (f) can be manufactured by, for instance, the following methods. In the first manufacturing method, after an absorbent material constituting the second region R2 is deposited, an absorbent material constituting the first region R1 and SAP are deposited on the absorbent material constituting the second region R2. Then, the whole surface of the laminated absorbent materials is pressed in a thickness direction to thereby form the absorber with a uniform thickness. Further, in the second manufacturing method, absorbent material is deposited, and a thickness of the absorbent material as a part defined as the first region S1 is made thinner than that of the absorbent material within its surrounding region (the second region). Yet further, SAP is mixed in the absorbent material as a part defined as the first region R1. Subsequently, the whole surface of the laminated absorbent material is pressed in the thickness direction to thereby form the absorber with a uniform thickness. With such a structure, the absorber shown in FIGS. 8 (e) and 8 (f) can be manufactured.

FIGS. 8(g) and 8(h) illustrate an absorber 40K according to a fourth modification. FIG. 8(g) is a plan view, and FIG. 8(h) is a cross-sectional view of a cross-section along the longitudinal direction in the center of the absorber in the widthwise direction.

The absorber 40K according to the fourth modification is configured from a substantially hourglass shaped layer. The first region R1 is configured from the intermittent disposition of the absorbent polymer. For example, the first region R1 is defined by an absorbent sheet, such as the absorbent sheet 90, disposed on the skin contact surface side of the back waistline region S2. The absorber has a low basis weight region 47, for function as the body fluid guide unit and the curving unit, formed along the longitudinal direction.

Other Embodiments

As mentioned above, although several embodiments of the present invention have been disclosed, the descriptions and drawings that form a portion of this disclosure are not to be considered as limitation to the present invention. From this disclosure, a variety of alternate embodiments, examples, and applicable techniques will become apparent to one ordinarily skilled in the art.

For example, in the above embodiments, a pants-type disposable diaper was explained, however, the present invention is not limited thereto, and can be applied to an open-type disposable diaper, incontinence pad, sanitary napkin and other types of absorptive products.

In the aforementioned embodiments, the absorber was configured to be curved by using slits, elastic members, and/or boundary portions where the rigidity changes, however, the absorber can also be configured to be curved by reducing the thickness of the absorber and by performing embossing in the absorber.

The absorbent article according to the aforementioned embodiments is provided with the side end elastic member 49, but the side end elastic member 49 may also not be provided in further embodiments. The leakage-preventing wall that has an upstanding part (the leakage-preventing elastic member 53) for preventing side leakage from the crotch may be omitted in some embodiments.

In aforementioned embodiments, the absorber 40 has a bi-layered structure of the first layer 41 and the second layer 42, but the absorber 40 of the worn article according to further embodiments may be configured from a single layer or may be configured from three or more layers.

In aforementioned embodiments, the central curving unit and the first curving unit are provided, but a plurality of curving units, such as a second curving unit and a third curving unit, may also be provided outboard of the first curving unit in the widthwise direction in some embodiments.

Further, in aforementioned embodiments, the leg gathers have been provided so as not to laterally cross the absorber, but a leg holes elastic member for the left leg and a leg holes elastic member for the right leg may also be provided continuously so as to laterally cross the absorber in some embodiments.

The third modification illustrates an example where the first region is formed by giving a greater basis weight of the absorbent polymer to one portion of the one-layered absorber, but, in some embodiments, the absorbent polymer may be disposed on the absorber in the center part in the widthwise direction, or the absorbent polymer may be disposed over substantially the entire width of the absorber in the widthwise direction, or the absorbent polymer may be scattered on the surface of an absorber.

As described above, needless to say, the present invention includes various embodiments and the like not described here. Accordingly, the scope of the present invention is defined only by the appended claims in view of the above description.

The entire contents of Japanese Patent Application No. 2011-195207 (filed on Sep. 7, 2011) are incorporated in the present specification by reference.

INDUSTRIAL APPLICABILITY

According to the characteristic provided by some embodiments of the present invention, it is possible to provide disposable wearing article by which absorption performance can be ensured and, at the same time, deterioration in absorption performance can be prevented by improving the fit in the proximity of the crotch portion of the wearer.

Consequently, the urination region functions as an in-drawing region for drawing in the bodily fluid and the buttocks region functions as a holding region for holding the bodily fluid, each being able to fulfill the respective function. Accordingly, deterioration in absorption performance can be prevented.

Disposing the absorbent polymer between the topsheet and the absorber in the buttocks region makes it possible for bodily fluid to be held by the absorbent polymer, thus preventing reversal of liquid, even in a case where pressure due to the weight of the hindquarters is applied.

REFERENCE SIGNS LIST

1 . . . Disposable diaper (disposable wearing article); 3 . . . Waist gathers; 3A . . . Waist elastic member; 4, 4' . . . Front waistline side edge; 5 . . . Leg gathers; 5F . . . Foreside leg-holes elastic member; 5R . . . Rear leg-holes elastic member; 6, 6' . . . Back waistline edge; 8 . . . middle inside leg edge; 10 . . . Topsheet; 15 . . . Auxiliary sheet; 30 . . . Absorber backside covering sheet; 40, 40G, 40H, 40J, 40K . . . Absorber; 41 . . . First layer;

41W . . . Inner end; 42 . . . Second layer; 42W . . . Outer end; 43 . . . Elastic member covering sheet; 44 . . . Central elastic member; 45 . . . Central aperture; 46 . . . First side slit; 47 . . . Low basis weight region; 49 . . . Side end elastic member; 53 . . . Leakage-preventing elastic member; 60 . . . Sidesheet; 70F . . . Foreside exterior topsheet; 70R . . . Backside exterior topsheet; 80F . . . Foreside exterior backsheet; 80R . . . Backside exterior backsheet; 90 . . . Absorbent sheet; 92 and 93 . . . Liquid-permeable sheet; 96 . . . Absorbent polymer containing region; 97 . . . Absorbent polymer non-containing region; 1000 . . . Exterior center sheet; 110 . . . Intermediate region; R1 . . . First region; R2 . . . Second region; S1 . . . Front waistline region; S2 . . . Back waistline region; S3 . . . Urination region

The invention claimed is:

1. A disposable wearing article, comprising:
   a liquid-permeable topsheet;
   a backsheet;
   an absorber disposed between the topsheet and the backsheet, the absorber having a longitudinal direction, a widthwise direction orthogonal to the longitudinal direction, an inner direction for facing a wearer, and an outer direction opposite to the inner direction;
   a urination region, which is adapted to be in contact with a urination unit of the wearer;
   a buttocks region, which is disposed rearwardly of the urination region and is adapted to be in contact with buttocks of the wearer; and
   an absorbent sheet which includes an absorbent polymer sandwiched between liquid-impermeable layers and is provided between the topsheet and the absorber;
   wherein
   the absorber has a curving unit in at least the urination region to cause the absorber to curve convexly in the inner direction,
   the absorbent sheet is disposed in the buttocks region, but not in the urination region,
   the buttocks region includes at least one polymer containing region in which the absorbent polymer is disposed,
   the curving unit is positioned forward of the at least one polymer containing region,
   the curving unit is elongated in the longitudinal direction, and
   the curving unit includes a curving unit stretchable member stretchable in the longitudinal direction.

2. A disposable wearing article, comprising:
   a liquid-permeable topsheet;
   a backsheet;
   an absorber disposed between the topsheet and the backsheet, the absorber having a longitudinal direction, a widthwise direction orthogonal to the longitudinal direction, an inner direction for facing a wearer, and an outer direction opposite to the inner direction;
   a urination region, which is adapted to be in contact with a urination unit of the wearer;
   a buttocks region, which is disposed rearwardly of the urination region and is adapted to be in contact with buttocks of the wearer,
   wherein
   the absorber has first and second regions having an absorbent polymer, and wherein a basis weight of the absorbent polymer in the second region is lower than a basis weight of the absorbent polymer in the first region,
   the absorber has a curving unit in at least the urination region to cause the absorber to bend convexly in the inner direction,
   the second region is in the urination region,
   the first region is on a top side of the absorber in the buttocks region,
   the buttocks region includes at least one polymer containing region in which the absorbent polymer is disposed,
   the curving unit is positioned forward of the at least one polymer containing region,
   the curving unit is elongated in the longitudinal direction, and
   the curving unit includes a curving unit stretchable member stretchable in the longitudinal direction.

3. The disposable wearing article according to claim 1, wherein the curving unit further comprises at least one of:
   a slit formed in the absorber;
   a low basis weight region in the absorber, and having a lower basis weight than a further region of the absorber, the further region surrounding the low basis weight region; or
   a compressed region of the absorber.

4. The disposable wearing article according to claim 1, wherein the buttocks region includes a buttocks stretchable member stretchable in at least the longitudinal direction.

5. The disposable wearing article according to claim 4, wherein the buttocks stretchable member includes a pair of leg-holes stretchable members adapted to be disposed around the legs of the wearer.

6. The disposable wearing article according to claim 1, wherein the buttocks region includes a waistline elastic member which is adapted to be disposed around the waist of the wearer and is stretchable in the widthwise direction.

7. The disposable wearing article according to claim 1, wherein
   the buttocks region further includes a polymer non-containing region where the absorbent polymer is not disposed; and
   the polymer non-containing region is provided between adjacent polymer containing regions among the plurality of polymer containing regions.

8. The disposable wearing article according to claim 1, wherein the curving unit extends in the urination region and in the buttocks region.

9. The disposable wearing article according to claim 4, wherein the buttocks stretchable member is further stretchable in the widthwise direction.

10. The disposable wearing article according to claim 8, wherein the at least one polymer containing region defines a V-shape where an apex of the V-shape is directed rearwardly in the longitudinal direction.

11. The disposable wearing article according to claim 1, wherein
    the curving unit further includes a central aperture,
    the central aperture is formed in a center of the absorber in the widthwise direction, and
    the curving unit stretchable member overlaps the central aperture in the thickness direction of the disposable wearing article.

12. The disposable wearing article according to claim 1, wherein the at least one polymer containing region includes a plurality of polymer containing regions.

13. The disposable wearing article according to claim 1, wherein the curving unit stretchable member is a central elastic member on a center longitudinal line that bisects a width of the absorber in the widthwise direction.

* * * * *